(12) United States Patent
Skigen

(10) Patent No.: US 9,192,572 B2
(45) Date of Patent: Nov. 24, 2015

(54) ORAL ANESTHESIA APPLICATION

(71) Applicant: Andrew L. Skigen, Jacksonville, FL (US)

(72) Inventor: Andrew L. Skigen, Jacksonville, FL (US)

( * ) Notice: Subject to any disclaimer, the term of this patent is extended or adjusted under 35 U.S.C. 154(b) by 0 days.

(21) Appl. No.: 13/732,408

(22) Filed: Jan. 1, 2013

(65) Prior Publication Data

US 2013/0315842 A1 Nov. 28, 2013

Related U.S. Application Data

(60) Provisional application No. 61/582,453, filed on Jan. 2, 2012.

(51) Int. Cl.
*A61K 49/00* (2006.01)
*A61K 9/00* (2006.01)
*A61K 9/70* (2006.01)

(52) U.S. Cl.
CPC ............... *A61K 9/0056* (2013.01); *A61K 9/006* (2013.01); *A61K 9/0034* (2013.01); *A61K 9/7007* (2013.01)

(58) Field of Classification Search
CPC ... A61K 9/006; A61K 9/7007; A61K 9/0056; A61K 9/0034
See application file for complete search history.

(56) References Cited

U.S. PATENT DOCUMENTS

| 4,529,601 | A | * | 7/1985 | Broberg et al. | 514/626 |
| 5,466,465 | A | * | 11/1995 | Royds et al. | 424/449 |
| 6,620,852 | B2 | * | 9/2003 | Brogan et al. | 514/626 |
| 2005/0014823 | A1 | * | 1/2005 | Soderlund et al. | 514/536 |
| 2005/0136112 | A1 | * | 6/2005 | Gonzales et al. | 424/473 |

OTHER PUBLICATIONS

Primosch et al, "Comparison of topical EMLA 5% oral adhesive to benzocaine 20% on the pain experienced during palatal anesthetic infiltration in children," American Academy of Pediatric Dentistry, 2001, vol. 23, pp. 11-14.*

* cited by examiner

*Primary Examiner* — Suzanne Ziska
(74) *Attorney, Agent, or Firm* — Joseph P. Kincart; Ideation Law, PLLC

(57) ABSTRACT

The present invention provides methods of administering an active agent to a localized mucous membrane in the oral cavity of a mammal, as well as oral dissolving film formed therefore.

7 Claims, 4 Drawing Sheets

301

302

ORAL ANESTHESIA APPLICATION

CROSS REFERENCE TO RELATED APPLICATIONS

The present application claims priority to U.S. Patent Application Ser. No. 61/582,453 entitled: Oral Anesthesia Application, and filed Jan. 1, 2012, as a Continuation in Part Application, the contents of which are relied upon and incorporated herein by reference.

FIELD OF THE INVENTION

The present invention relates to methods and apparatus for topically applying medicaments within the human oral cavity. More specifically, the present invention presents methods an apparatus for providing anesthesia to the human gum or other oral tissue in a pain free fashion.

BACKGROUND OF THE INVENTION

Dental fear refers to the fear of dentistry and of receiving dental care. It is estimated that as many as 75% of US adults experience some degree of dental fear, from mild to severe. It is further estimated that some 5 to 10 percent of U.S. adult dental patients are considered to experience dental phobia wherein they become so fearful of receiving dental treatment that they avoid dental they have a dental emergency, such as a toothache or dental abscess. Women tend to report more dental fear than men, and younger people tend to report being more dentally fearful than older individuals. In addition People tend to report being more fearful of more invasive procedures, such as oral surgery which require anesthesia in order to manage pain, than they are of less painful treatments, such as professional dental cleanings, or prophylaxis.

Direct experience is the most common way people develop dental fears. Significant numbers of people report that dental fear is related to painful dental experience. Often a painful experience begins with administration of a local anesthetic via injection into very sensitive oral tissue, such as gum tissue. Once anesthesia is administered, patient pain may be controlled and proper dental care may be carried out.

What is needed therefore is a way to easily administer at least a first dose of local anesthesia in a manner which does not induce pain to the patient and therefore decrease the incidence of patient pain and patient anxiety.

Traditionally, oral dissolving films have not been helpful to address this problem. Although oral dissolving films have been known to be placed on a patient's tongue or any oral mucosal tissue. Such films are for systemic delivery of an active agent, entering the blood stream via the digestive track.

SUMMARY OF THE INVENTION

Accordingly, the present invention provides methods and products for painlessly administering anesthetic agents in very specific topical areas of the oral cavity. In particular, oral thin films are sized and shaped to adhere to areas of a mammalian gum and release an anesthetic agent to the area of the gum to which they are adhered. The oral thin films may include, for example, orally dissolving films (ODFs) which provide quick release of an active pharmaceutical ingredient (API) when placed on a moist mucosal surface.

Unlike previously known applications which placed an orally dissolving thin film on a patient's tongue or other oral mucosal tissue for general administration of an active agent via the digestive canal. The present invention provides for rapid adherence of the film to mucosal tissue and direct administration of an anesthetic agent directly to the site of adherence. In general, the film is placed on a gum or other mucosal tissue and hydrated with saliva; the saliva hydration causes adherent forces to bind the specifically sized ODF on to a site of anesthetic application, or other delivery of an active agent. The anesthesia is administered directly into the adhesion site on the gum.

As the ODF dissolves, traditional local anesthesia, such as an injection of Novocain may be administered directly into the gum site that has been anesthetized by the anesthetic agent of the ODF.

DETAILED DESCRIPTION

The present invention provides methods and products for locally administering one or more active agents to a mucous membrane such as, for example, mucous membrane included in a mammalian oral cavity. The active agent may include, for example an anesthetic. Some specific examples include an active agent including ethyl ester of p-amino benzoic acid (PABA), such as, for example, benzocaine. Other examples may include, but are not limited to: benzocaine, butamben, dibucaine, lidocaine, oxybuprocaine, pramoxine, proparacaine, proxymeta caine, and tetracaine (also named amethocaine). In general, according to the present invention, a film with an active agent is placed upon a mucous membrane and an area of the mucous membrane is anesthetized such that a procedure, such as an injection, may be administered to the anesthetized area.

Other exemplary areas of mammalian mucous membrane may include, but not be limited to a mammalian vaginal cavity. Other procedures may include a biopsy or other minor incision. A biopsy or incision may include, by way of example a cervical biopsy which may be painful without anesthesia.

Glossary

Orally Dissolving Films (sometimes referred to herein as "ODF") as used herein shall mean a non-toxic film which may be placed in an mammalian oral cavity and dissolve as a result of contact with saliva or other liquid on of secreted by the mucous membrane comprising the mammalian oral cavity.

In various embodiments, ODFs may contain, by way of teaching example one or more of: film-forming polymers such as hydroxypropylmethyl cellulose (HPMC), hydroxypropyl cellulose (HPC), pullulan, carboxymethyl cellulose (CMC), pectin, starch, polyvinyl acetate (PVA), and sodium alginate.

An ODF according to the present invention may additionally include supplementary ingredients such as, by way of example: plasticizers, sweetening and flavoring agents, coloring agents, saliva-stimulating agents, and thickening agents. Inactive ingredients of may include: Methocel K3, Methocek K100, Methocel K4, Sodium Carboxymethyl Cellulose, Glycerine, Sucralose, Polysorbate 80, Peppermint Oil Flavor, Gum Arabic, Sodium Copper Chlorophylin.

Oral Cavity Based Size and Shape (sometimes referred to herein as "OCBSS" as used herein shall mean a size and shape of an ODF suitable for placement on the surface of a mucous membrane and/or gum comprising a mammalian oral cavity.

Figure 1:
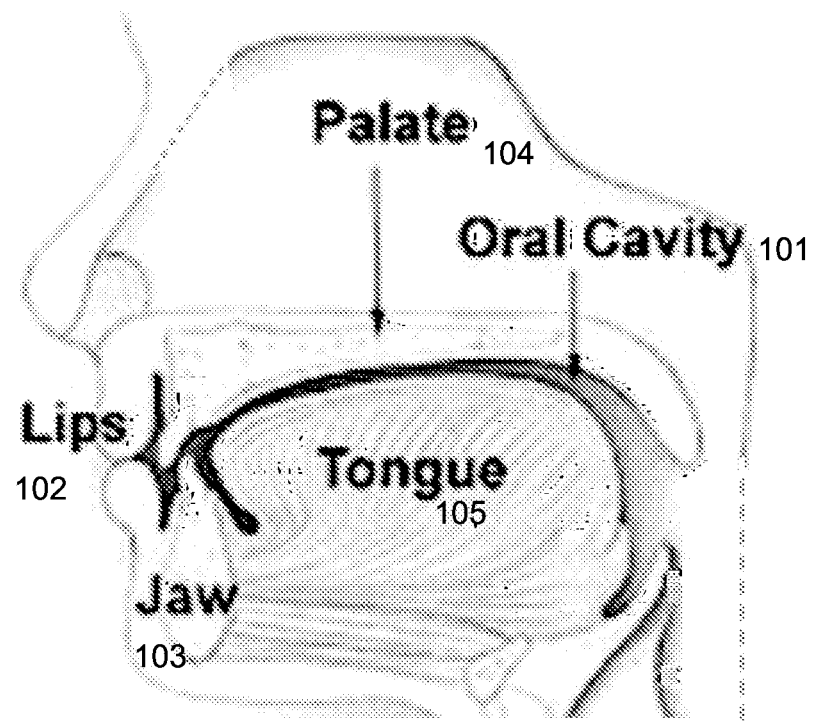
FIG. 1 illustrates an oral cavity in which the present invention may be implemented.

Referring now to FIG. 1, a cutaway of a profile of a mammalian oral cavity 101 (as illustrated a human oral cavity) is illustrated. The mammalian oral cavity 101 may be bordered for example by a set of lips 102, a palate 103 and a jaw 104. The mammalian oral cavity will also contain a tongue 105, and gums and teeth (illustrated in FIG. 2).

Figure 2:
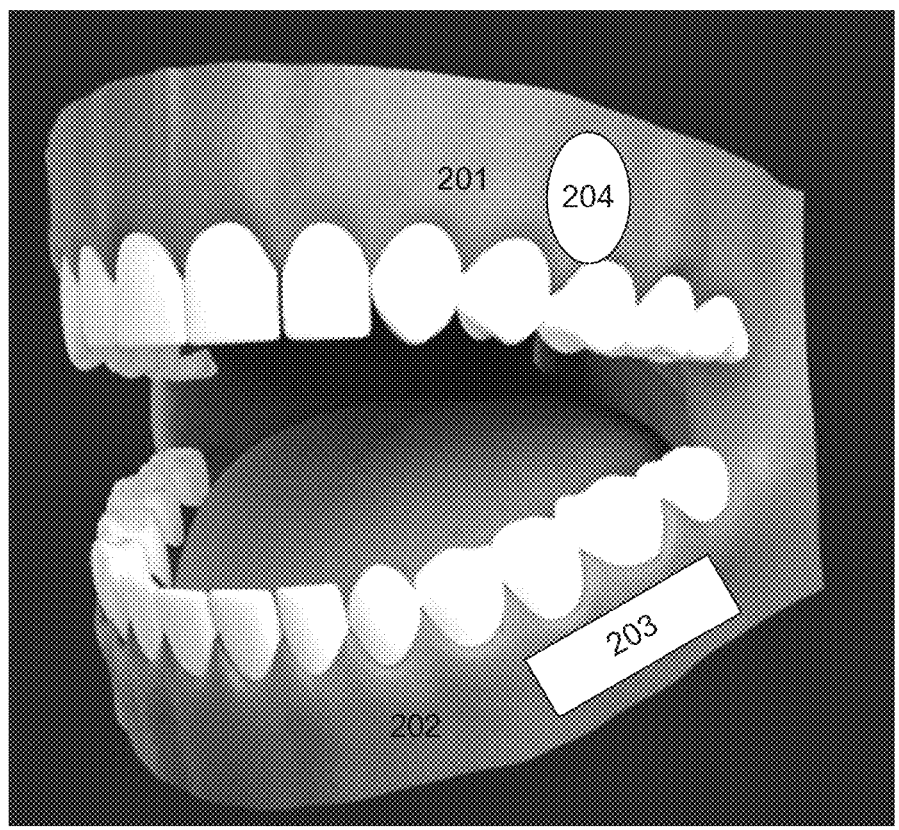
FIG. 2 illustrates a human upper gum and lower gum with locally administrating ODF strips according to some embodiments of the present invention.
Figure 3:
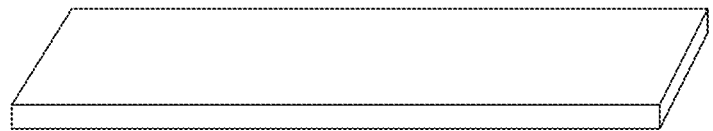
FIG. 3 illustrates rectangular shape and oval shape implementations according to some embodiments of the present invention.
Figure 3:
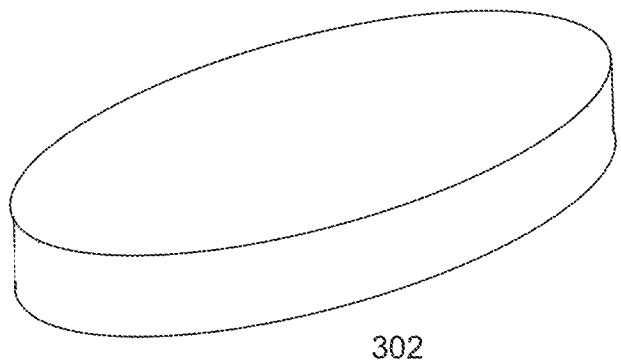

Referring now to FIG. 2, a perspective view of human upper gums 201 and lower gums 202 are shown. As illustrated, the upper gums 201 have an oval shaped ODF 203 placed on gum surface. In addition, the lower gums 203 have a rectangular ODF placed upon the gum surface. As illustrated, each of the oval shaped ODF 203 and the rectangular shaped ODF 204 are Oral Cavity Based Size and Shape since each sits on a gum and do not protrude beyond a gum line on to the teeth Referring now FIG. 3, perspective views of exemplary shapes of Oral Cavity Based Shapes are illustrated. Illustrated shapes include, by way of example, rectangular 301 and oval 302. Other shapes are also within the scope of the present invention. In some embodiments, an ODF may be one or both of: shaped and sized with a scissor prior to placement on a gum or mucous membrane. Placement may be accomplished via a human finger or a swab or other instrument.

Figure 4:
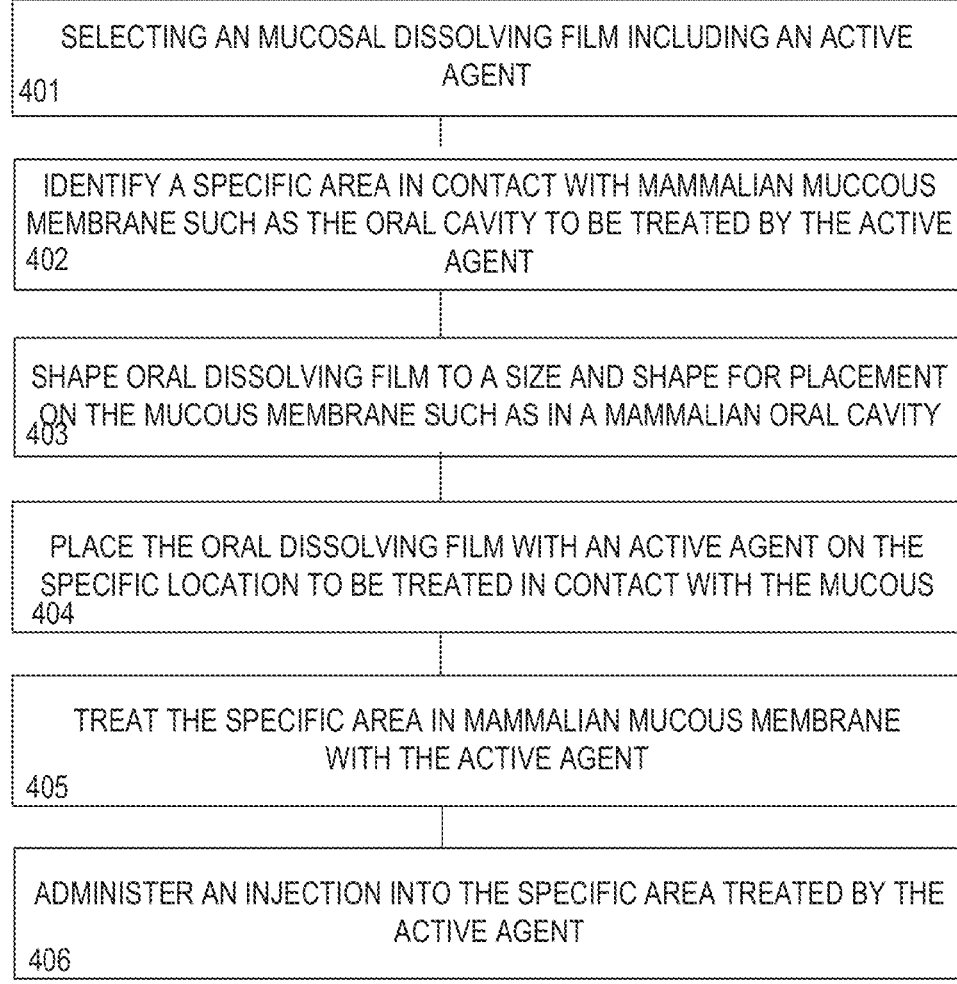
FIG. 4 illustrates method steps that may be practiced in some implementations of the present invention.

Referring now to FIG. 4, exemplary steps that may be practiced in some embodiments of the present invention are illustrated. The steps are presented in a logical order for some embodiments, however, the order presented is by way of example only and not meant to limit the scope of the invention. At 401, an active agent may be included in an ODF. At 402, a specific location or area within a mammalian cavity to be anesthetized or otherwise treated by an active agent included within the ODF. At 403, the ODF may be sized and shaped such that it is suitable for placement on the specific location or area identified. At 404, the ODF which has been shaped is placed at the desired location to be treated. At 405, the specific location or area in the mammalian oral cavity which be treated received the effect of the active agent.

At 406, an injection may be administered into the specified area. In some embodiments, an injection may include additional anesthesia.

In some embodiments, the OFG includes an active agent which includes a pharmaceutical ingredient. The pharmaceutical ingredient may be absorbed at the specified location for local oral administration as opposed to systemic active pharmaceutical ingredient.

According to some embodiments, the active pharmaceutical ingredients may include those known to topically treat oral conditions such as, by way of non-limiting example, one or more of: anesthetics, antifungal; antiseptics; and topical steroids.

According to the present invention, the nature of the film that is included in the ODF fixates the location of active pharmaceutical ingredient, eliminating migration, dissipation and dilution. The adhesion may be described as muco-adherence, wherein muco-adherence allows for a lower concentration of a given active pharmaceutical ingredient to be used to achieve a desired amount of anesthetic action and/or a desired health benefit.

Generally, lower concentration of an active agent may be beneficial due to a decrease in deleterious systemic side effects of excessive active pharmaceutical ingredient absorption such as methemaglobinemia or excessive exogenous steroids.

In some embodiments, and ODF may include a coloring agent to provide a visual indication of when the ODF dissolves and also a visual indication of which of the oral mucosa has been treated for easier identification of a treated area. Coloring agents may include, for example, a substance that allows a practitioner to identify an area that has been treated by an active agent, such as an anesthetic, whereby an injection may be administered into the area that has been made numb by anesthetic.

Coloring agents may include any benign coloring that is visible to a practitioner who will administer an injection. Accordingly, coloring agents may include by way of non-limiting example, natural pigments derived from natural sources such as vegetables, minerals or animals. Including: annatto, beet extract, caramel, beta-carotene and grape skin extract.

Other examples of coloring agents may include: Caramel coloring (E150), or other coloring made from caramelized sugar; Annatto (E160b), a reddish-orange dye or other coloring made from the seed of the achiote; Chlorophyllin (E140), a green dye or other coloring made from *chlorella* algae; Cochineal (E120), a red dye or other coloring derived from the cochineal insect, *Dactylopius coccus*; Betanin (E162) or other coloring extracted from beets; Turmeric or other coloring derived from curcuminoids, E100; Saffron or other coloring derived from carotenoids, E160a; Paprika (E160c); Lycopene (E160d); Elderberry juice; Pandan a green coloring or other coloring derived *Pandanus amaryllifolius*; Butterfly pea a blue dye or other coloring derived from *Clitoria ternatea*.

Other Coloring agents may include coloring approved under the Pure Food and Drug Act including, but not limited to: FD&C Blue No. 1—Brilliant Blue FCF, E133 (blue shade); FD&C Blue No. 2—Indigotine, E132 (indigo shade); FD&C Green No. 3—Fast Green FCF, E143 (turquoise shade); FD&C Red No. 40—Allura Red AC, E129 (red shade); FD&C Red No. 3—Erythrosine, E127 (pink shade, commonly used in glace cherries); FD&C Yellow No. 5—Tartrazine, E102 (yellow shade); and FD&C Yellow No. 6—Sunset Yellow FCF, E110 (orange shade).

In some preferred embodiments, the ODF with an active agent includes a film that is colored, so that when the ODF dissolves, the treated oral mucosa is easily identified.

The ODF may also be stored in aseptic packaging, limiting cross contamination and include flavoring which is pleasant to taste.

In some embodiments, exemplary ODFs may contain film-forming polymers such as hydroxypropylmethyl cellulose (HPMC), hydroxypropyl cellulose (HPC), pullulan, carboxymethyl cellulose (CMC), pectin, starch, polyvinyl acetate (PVA), and sodium alginate.

Additional ingredients that may be included in various embodiments include one or more of: plasticizers, sweetening and flavoring agents, coloring agents, saliva-stimulating agents, and thickening agents. In some preferred embodiments, inactive ingredients may include: Methocel K3, Methocek K100, Methocel K4, Sodium Carboxymethyl Cellulose, Glycerine, Sucralose, Polysorbate 80, Peppermint Oil Flavor, Gum Arabic, and Sodium Copper Chlorophylin.

Active agents may also include, for example a vitamin treatment, a nutraceutical, a nutrient, an antimicrobial or antibacterial agent.

EXAMPLES

In vitro and in vivo studies were conducted to gauge the effectiveness of a novel oral mucosa adhesive, moderately water-soluble, pliant polymer artificial dentifrice (AD) film containing dibucaine (DC) for relief of pain due to oral erosion. The film was prepared from a hydroxypropyl cellulose-M (HPC-M) ethanol solution containing varying amounts of DC, as well as polyethylene glycol.

In the in vitro experiments, the disintegration of HPC-M showed a lag time of about 50 min, a much lower rate than that of drug release, which more or less leveled off after 50 min. Twenty-five percent of the DC was released from the film (0.113 and 0.225 mg/cm2) after the initial 5 min, which then reached about 80% after 50 min, the time at which the polymer began to break up. In the in vivo study, the local anesthetic effect of the film was evaluated in 23 patients (10 males, 13 females) suffering from the adverse effects of chemotherapy. When applied to the wet surface of the mucosa, the AD film absorbed moisture and showed excellent adhesion. Pain relief in patients lasted 2.2+/−0.21 and 4.3+/−0.25 h at DC doses of 0.113 and 0.225 mg/cm2, respectively. These results suggest that the AD film may cover mucositis sites of oral mucosa long enough to allow DC release and bring relief from pain arising from chemotherapy and/or radiotherapy.

2. Pediatr Dent. 2001 January-February; 23(1):11-4.

Comparison of topical EMLA 5% oral adhesive to benzocaine 20% on the pain experienced during palatal anesthetic infiltration in children.

Primosch R E, Rolland-Asensi G.

Department of Pediatric Dentistry, University of Florida College of Dentistry, Gainesville, Fla., USA. rprimosch@dental.ufl.edu Example 1

PURPOSE: The purpose of this investigation was to compare the pain responses of children during local anesthetic infiltration at bilateral palatal sites prepared with the topical application of benzocaine 20% oral adhesive (Orabase-B) versus benzocaine 20% gel (Hurricaine) or EMLA 5% oral adhesive (EMLA 5% cream in Orabase Plain).

METHODS: Forty subjects, aged 7-15 years old, received bilateral palatal injections following topical application of anesthetic agents applied in a randomized, crossover design. Pain responses were compared based upon subject self-report using a visual analogue scale (VAS), changes in the subject's heart rate, and operator assessment using a modified Children's Hospital of Eastern Ontario Pain Scale (CPS) that rated behavioral changes in children. Following the injections, the subjects were asked to choose which agent was preferred based on comfort and taste acceptance.

RESULTS: All the agents tested were equivalent in injection pain response comparisons, but Hurricaine had a slight advantage in expressed subject preference and taste acceptance over the other topical anesthetic agents tested.

Example 2

Clinical evaluation of MGI 209, an anesthetic, film-forming agent for relief from painful oral ulcers associated with chemotherapy.

LeVeque F G, Parzuchowski J B, Farinacci G C, Redding S W, Rodu B, Johnson J T, Ferretti G A, Eisenberg P D, Zimmer M B.

Harper Hospital, Detroit, Mich. 48201.

PURPOSE: This open-label, multicenter trial evaluated the efficacy of a muco-adherent, anesthetic medication (MGI 209) for relief from painful oral ulcers associated with cytotoxic chemotherapy.

PATIENTS AND METHODS: Twenty-eight eligible cancer patients who had up to five discrete oral ulcers (total area<or=5 cm2) completed this study. Mean age was 53.5 years (range, 21 to 81). Subjective assessments of oral discomfort before and after an orange juice pain challenge (OJPC), which was measured using a visual analog scale (VAS), and visual estimates of the amount of MGI 209 that remained on treated ulcers were collected at (1) baseline (before MGI 209 treatment); and (2) 30, 60, 120, and 180 minutes post treatment.

RESULTS: Most subjects had low VAS scores (4 or less), which was indicative of oral discomfort, at baseline before and after the OJPC. At 30, 60, 120, and 180 minutes after MGI 209 treatment, most subjects had high VAS scores before and after an OJPC compared with baseline scores, which was indicative of a substantial increase in oral comfort; these differences were statistically significant (P<0.0001). Mean percent of MGI 209 estimated to remain on ulcers at the previously mentioned times was 93.7%, 90.3%, 79.6%, and 71.3% of the total amount applied, respectively.

Example Conclusion: Benzocaine hydrochloride in combination with the protective, muco-adherent film-coating relieved discomfort for at least 3 hours even with exposure to an irritating beverage. MGI 209 treatment should allow patients with chemotherapy-induced oral ulcers to drink and eat with significantly diminished pain or no pain.

Conclusion

The present invention, as described above and as further defined by the claims below, provides methods of administering an active agent to a localized mucous membrane in the oral cavity of a mammal, as well as ODR formed therefore. The exemplary style of describing is not meant to limit the scope of the invention and the invention is therefore more clearly described and limited by the claims below.

What is claimed is:

1. A method of applying an active agent to a specific site on a mammalian mucous membrane, the method comprising the steps of:
   selecting an oral dissolving film comprising a local anesthetic active agent and a coloring agent;
   identifying a specific area on the mammalian mucous membrane for treatment by the active agent wherein the mucous membrane comprises tissue within an oral cavity;
   placing the oral dissolving film comprising the local anesthetic active agent and the coloring agent on the identified area;
   anesthetizing the identified area with the local anesthetic active agent following the placement of the oral dissolving film on the identified area;
   dissolving the oral dissolving film essentially in its entirety;
   generating a visual indicator on the identified area of the mammalian mucous membrane with the coloring agent wherein the visual indicator remains on the mucous membrane following the dissolving of the oral dissolving film essentially in its entirety; and
   treating the area on the mammalian mucous membrane comprising the visual indicator, wherein the treating the mammalian mucous membrane comprising the visual indicator includes an injection into the mammalian mucous membrane.

2. The method of claim 1 wherein the active agent comprises a topical anesthetic and the injection comprises administration of an additional anesthetic into the specific area on the mammalian mucous membrane for treatment and the dissolving of the dissolvable film substantially in its entirety results from exposure of the dissolvable film to moisture in the oral cavity.

3. The method of claim 2 wherein the active agent comprises ethyl ester of p-aminobenzoic acid.

4. The method of claim 2 wherein the active agent comprises lidocaine.

5. The method of claim 1 wherein the coloring agent comprises one or more pigments derived from natural sources comprising a vegetable base.

6. The method of claim 1 wherein the visual indicator remains visible on an area of oral mucosa after the oral dissolving film dissolves essentially in its entirety.

7. The method of claim 6 wherein the visual indicator allows a practitioner to visually identify an area that has been treated by the local anesthetic and administer the injection into the area that has been treated by the local anesthetic with the oral dissolving film essentially dissolved in its entirety.

* * * * *